United States Patent [19]

Galwey et al.

[11] 4,426,621

[45] Jan. 17, 1984

[54] DETECTION CIRCUITRY FOR ELECTROCHEMICAL ANALYSIS

[75] Inventors: Ronald K. Galwey, Los Gatos; Kay K. Kanazawa, San Jose, both of Calif.

[73] Assignee: International Business Machines Corporation, Armonk, N.Y.

[21] Appl. No.: 278,801

[22] Filed: Jun. 29, 1981

[51] Int. Cl.³ .............................................. G01N 27/02
[52] U.S. Cl. ..................................... 324/439; 324/446; 204/406; 204/412
[58] Field of Search ........................ 324/439, 446, 438; 204/406, 412

[56] References Cited

U.S. PATENT DOCUMENTS

| | | | |
|---|---|---|---|
| 1,755,479 | 4/1930 | Jones | 324/439 |
| 3,486,998 | 12/1969 | Sellers et al. | 204/195 |
| 3,924,175 | 12/1975 | Wilson | 324/30 R |
| 4,059,406 | 11/1979 | Fleet | 23/230 R |
| 4,066,528 | 1/1978 | Mansfield | 204/195 T |
| 4,220,916 | 9/1980 | Zimmermann et al. | 324/446 |
| 4,227,988 | 10/1980 | Galwey et al. | 204/406 |
| 4,230,554 | 10/1980 | Blanke | 204/195 T |

Primary Examiner—Michael J. Tokar
Assistant Examiner—Kevin D. O'Shea
Attorney, Agent, or Firm—R. E. Cummins; G. E. Roush

[57] ABSTRACT

Analytical apparatus is arranged for increased sensitivity in determining a desired characteristic by decreasing the sensitivity to extraneous noise, essentially as common mode signal, while treating the desired signal differentially. Test signal is applied to apparatus comprising an electrochemical cell containing electrolyte in which a pair of matched working electrodes are equispaced from a counter electrode and from a reference electrode. The working electrodes conduct different values of current, the difference being a measure of characteristic of material making up the electrolyte. The signal applied between the counter and the working electrodes is varied over a predetermined range. The potential between the working electrodes is established at zero for basic operation, but a fixed biasing potential is established between the two working electrodes for a given experiment in which the test signal is varied. The biasing potential is usually relatively small and the current flow difference under study is likewise very small. The data output signal which is proportional to the small difference in the currents, is amplified in stable high gain circuitry.

2 Claims, 4 Drawing Figures

DETECTION CIRCUITRY FOR ELECTROCHEMICAL ANALYSIS

RELATED APPLICATIONS

The invention is related to that shown and described in copending U.S. Pat. application Ser. No. 187,120 of Ronald Keith Galwey and Kay Keiji Kanazawa filed on the Sept. 15, 1980, for "Servosystem Operating About Noise Component Error Signal", and now U.S. Pat. No. 4,348,632.

FIELD

The invention relates to methods of, and apparatus for, analytical electrochemical determination, and it particularly pertains to methods of increasing the sensitivity of apparatus used in such analysis.

BACKGROUND

Highly accurate analyses are required in the analytical laboratory for a great many purposes. The field of analysis of the electric parameters of chemical reactions is but one of a large number of studies. Many widely accepted, if not standard techniques have been developed. Frequently these techniques fail in one or more ways. For example in the use of the electrochemical cell, three significant factors presently limit the sensitivity of electrochemical apparatus for analytical determination:
1. Interfering currents arise from the charging of the "double layer capacitance" of the electrodes;
2. Random noise appears at the output of the current monitor resulting from stochastic phenomena in the potentiostat-cell system; and
3. Background faradaic currents arise.

A number of different approaches have been taken for enhancing the sensitivity of apparatus for trace analysis. Primarily these efforts have been made with respect to the first factor above.

PRIOR ART

The teaching of pertinent prior art is readily found in the following U.S. patents:

| | | | |
|---|---|---|---|
| 3,486,998 | 12/1969 | Sellers et al | 204/195 |
| 3,924,175 | 12/1975 | Wilson | 324/30R |
| 4,059,406 | 11/1977 | Fleet | 23/230R |
| 4,066,528 | 1/1978 | Mansfield | 204/195T |
| 4,230,554 | 10/1980 | Blanke | 204/195T |

The patents to Sellers et al and to Wilson, disclose simple electrochemical cells and current measuring circuitry attached thereto. The latter patent discloses two electrodes in a bath interconnected for measuring the polarization potential increment therebetween.

A detection circuit for electrochemical analysis is disclosed in the patent to Fleet, which circuit is entirely different in form from the subject invention and is assembled for another purpose.

The Mansfield and the Blanke patents each disclose electronic circuitry of interest in measuring the effects of a pair of electrodes immersed in the same electrolyte. Components and connections bear some similarity to that of the subject invention, but upon inspection it is seen that the arrangements are different and are for different analytical purposes, none of which involve determination based on differences in currents for working electrodes.

No one or any combination of the teachings in these patents will attain the circuit arrangement according to the invention for determining the difference in current flow by way of a matched pair of working electrodes in the same electrolytic bath.

SUMMARY

The objects of the invention referred to indirectly hereinbefore, and those that will appear as the specification progresses, are attained in apparatus comprising an electrochemical cell containing electrolyte in which a pair of matched working electrodes are equispaced from a counter electrode and from a reference electrode. The working electrodes in one embodiment of the invention are maintained at substantially equal, preferably ground potential, but conduct different values of current, the difference in current being a measure of a characteristic of material making up the electrolyte. According to the invention, the apparatus is arranged for increased sensitivity in determining the desired characteristic as compared to that obtained with prior art apparatus by decreasing the sensitivity to extraneous noise. Essentially this is accomplished by routing this extraneous noise as common mode signal while treating the desired signal differentially.

As with prior art apparatus, potential is established between the counter and the working electrodes. This potential is varied over a predetermined range. Preferably this potential is repeatedly varied with time so that a display can be activated and the results of the study viewed as a whole before precise measurement data are taken. The potential between the matched equispaced working electrodes is established at zero for basic operation. Preferably, according to the invention, a difference in potential between the two working electrodes is established. This difference in potential, or biasing potential, is fixed for a given experiment in which the counter potential varies in a range as hereinbefore mentioned. The biasing potential is usually relatively small. The current flow difference under study is likewise very small; thus the current flow through one working electrode is almost equal to that through the other electrode. The data output signal is proportional to the difference in the currents, which difference is amplified in high gain circuitry. Two or three operational amplifiers arranged for differential amplification of the currents through the working electrodes and rejection of the common mode currents are excellent for most analytical problems.

DRAWING

In order that all of the advantages of the invention obtain in practice, a preferred embodiment thereof, given by way of example only is described hereinafter with reference to the accompanying drawing, forming a part of the specification, and in which.

DESCRIPTION

Figure 1:
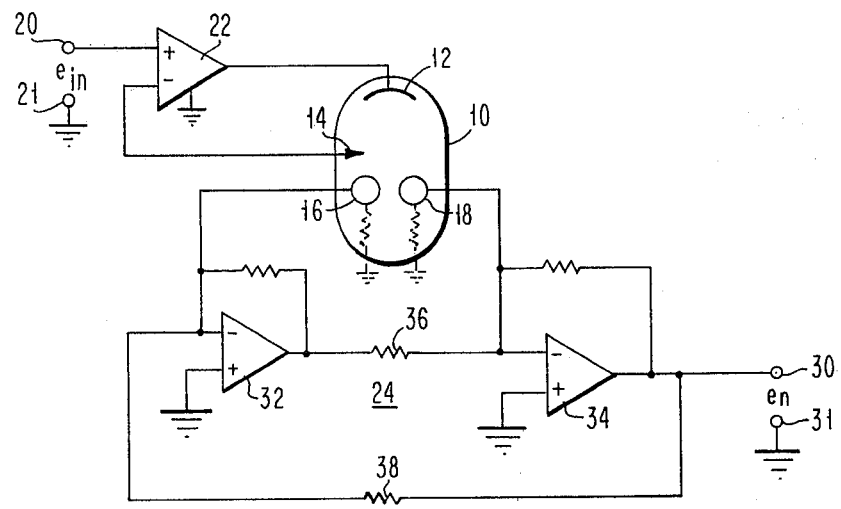
FIG. 1 is a schematic diagram of apparatus according to the invention illustrating fundamental relationships.
Figure 2:
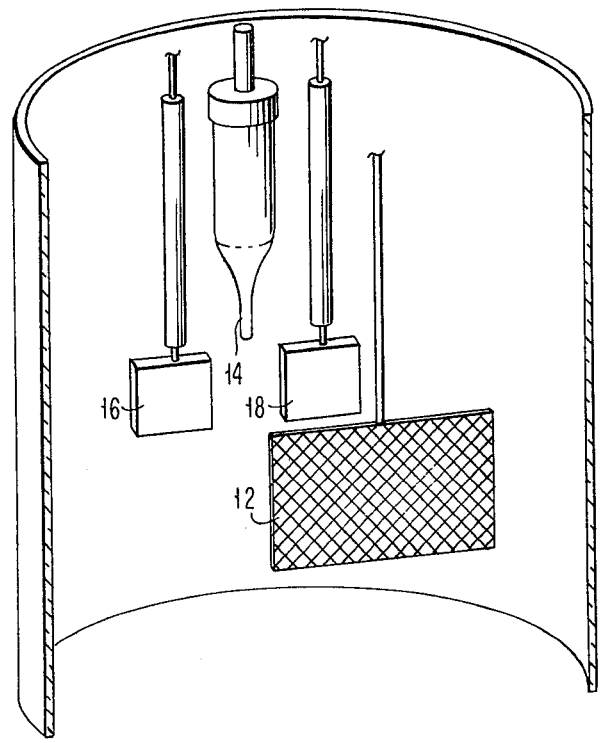
FIG. 2 is a schematic drawing illustrating an exemplary form of electrode arrangement in accordance with the invention.

An electrochemical analysis arrangement is shown schematically in FIG. 1 as comprising an electrochemical cell 10 having a counter electrode 12, a reference electrode 14, and two working electrodes 16 and 18, all immersed in the same solution. The cell structure follows conventional practice as desired except that the working electrodes 16 and 18 are identical and symmetrically placed with respect to the reference and counter electrode. A typical example of electrode placement is shown in FIG. 2. In this exemplary arrangement the working electrodes 16 and 18 define a plane and the reference electrode is arranged in the same plane midway between them. Alternately, the reference electrode 14 is placed anywhere in a plane midway of the two working electrodes and normal to the plane defined by the latter. The counter electrode 12 is arranged in a plane normal to the plane of the reference electrode locus and parallel to that defined by the working electrodes 16 and 18. While planar electrodes 12, 16 and 18 are shown, curved electrodes are alternative choices; it is only necessary that electrodes 16 and 18 be matched and equispaced with respect to the counter electrode 12.

Returning to FIG. 1, the cell 10 is filled with the electrolyte to be investigated. A testing potential $e_{in}$ is applied at input terminals 20, 21 of an input amplifier 22 and the results of the application translated by circuitry 24 appear as a potential $e_n$ at output terminals 30, 31. Further information relating to the application of testing signal at the terminals 20, 21 to the cell 10 will be found in U.S. Pat. No. 4,227,988, issued on the Oct. 14, 1980, for "An Improved Potentiostat for Use with Electrochemical Cells", and the copending U.S. Pat. application Ser. No. 49,525, filed on June 18, 1979, for "An Improved Instrument for Use with an Electrochemical Cell". The working electrodes 16, 18 are at substantially the same direct potential with respect to ground, which serves as the fixed reference potential point for the circuit.

The physical processes occurring at an electrochemical interface produce fluctuations of current through that interface under potentiostatic control. Studies of these noise sources permit investigations into the details of the physical processes. However, other sources of noise in the potentiostat/cell system often contribute such large random current noise as to effectively mask the interface noise of interest. These extraneous noise sources include, for example, Johnson noise, shot noise and flicker noise in the electronic components, shot noise and electrode junction noise in the cell.

According to the invention, circuitry is arranged for minimizing the effects of extraneous noise. The cell 10 is placed under potentiostatic control and the current difference between the two working electrodes 16, 18 is monitored by relatively quiet circuitry 24, having a minimum part count to keep extraneous electronic noise down. Operational amplifier 32 has one input terminal connected to the working electrode 16 and an output terminal connected to the working terminal 18, and one input terminal of another operational amplifier 34 by way of a resistor 36 while the output of the operational amplifier 34 is coupled by a resistor 38 to the working electrode 16 and the input terminal of the operational amplifier 32.

The requirements for the differencing circuitry 24 are that the current difference is obtained while maintaining both working electrodes at the same potential. In this case both electrodes are maintained at virtual ground. The differencing circuit 24 provides a voltage $e_n$ which is proportional to the current difference $i_A - i_B$. For typical circuit parameters, the sensitivity is on the order of ten microamperes per volt.

The current difference between two working electrodes 16, 18 which are at the same potential, contains none of the noise induced by the electronic noise in the potentiostat/cell control system. Double layer charging currents and faradaic currents also cancel and are not present in the current difference. The only noises present are those from the incoherent noise generated by the noise source of interest, i.e., the working electrode/solution interfaces and that incoherent noise generated by the current differencing circuitry, which noise is minimized by the circuitry 24.

Figure 3:
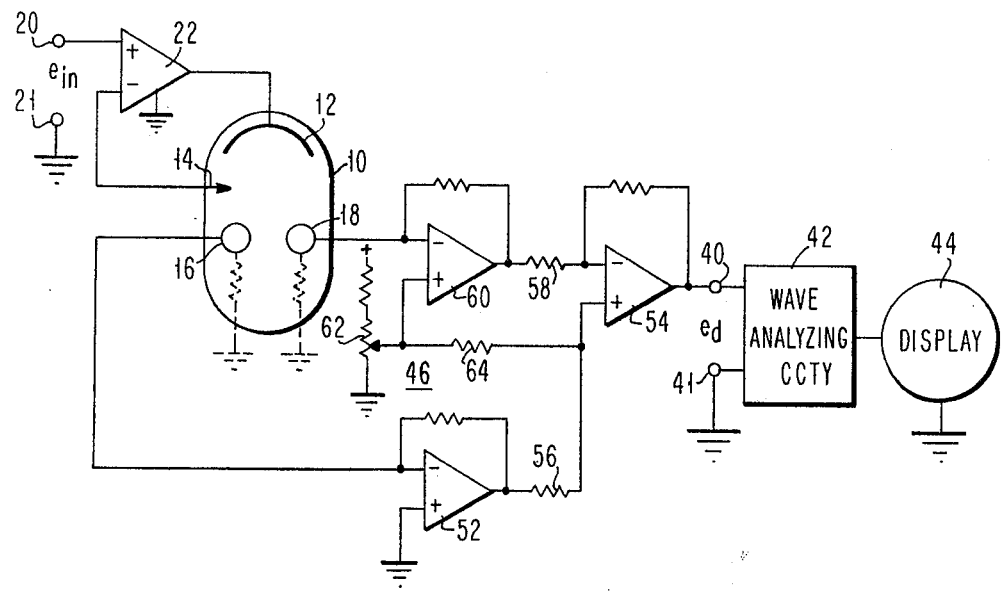
FIG. 3 is a schematic diagram of further apparatus according to the invention.

Additional data is obtained by the circuit arrangement shown in FIG. 3. Test potential $e_{in}$ applied at terminals 20, 21 results in a data signal at output terminals 40, 41. For convenience, wave analyzing circuitry 42 and a display 44 are coupled to the output terminals 40, 41, but form no part of the invention in and of itself.

The working electrode 16 is again connected to an input terminal of an operational amplifier 52, the output of which is applied to one input terminal of another operational amplifier 54 by way of a resistor 56. The other input terminal of the operational amplifier 54 is coupled through a resistor 58 and a differential amplifier 60 to the other working electrode 18. The latter is biased to a positive value with respect to the point of fixed reference potential, shown here as ground, by way of a potentiometer 62 of low resistance. A resistor 64 couples the arm of the potentiometer and the other input terminal of the differential amplifier 60 to the one input terminal of the operational amplifier 54, the output terminal of which is connected to the data output terminal 40.

Figure 4:
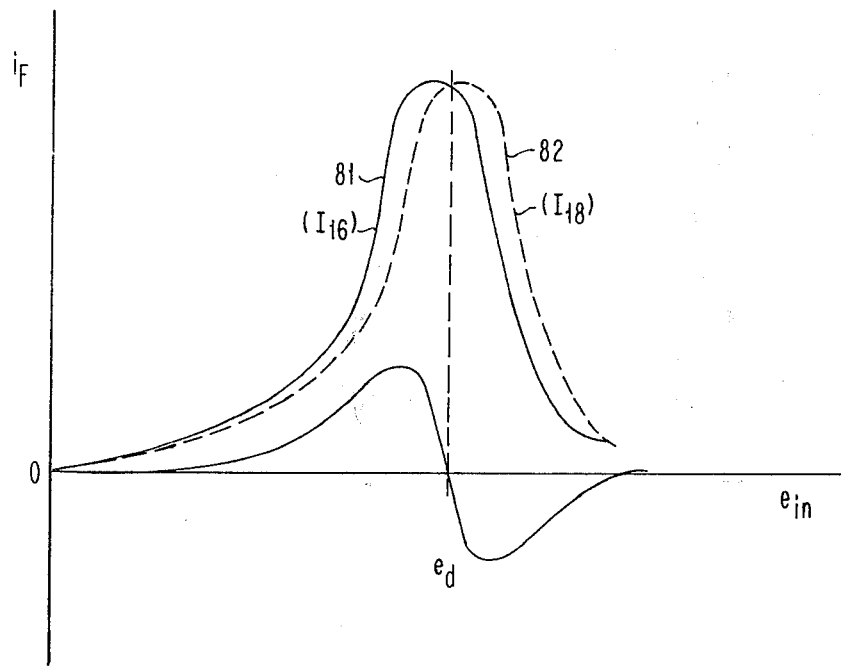
FIG. 4 is a graphical representation of current and potential relationships obtained with the apparatus according to the invention.

By adjusting the potentiometer 62, the working electrode 18 is altered in potential with respect to the other working electrode 16, but the overall circuitry 46, as the circuitry 24 of the previous embodiment, serves to produce an output potential $e_d$ which is proportional to the current difference between the working electrodes 16 and 18. This is graphically represented in FIG. 4, as though a trace on the display 44. The curves 81 and 82 represent the currents $I_{16}$ and $I_{18}$ of the working electrode as the test signal is varied. The two current waves are displaced by the bias obtained by manipulation of the potentiometer 62. The current waves are usually substantially identical, so that this method of separation is of decided advantage. With circuitry 46, the data signal $e_d$ is readily evaluated by the sharp angle at which it crosses the zero axis.

The circuitry described is sufficient for certain continuous techniques such as cyclic voltammetry, fundamental and harmonic AC voltammetry. The usual additional circuitry, such as timing, sampling and holding circuitry which is required for square wave and pulsed techniques, will be readily added by those skilled in the art.

The two independent working electrodes are of the same materials and approximately the same macroscopic geometrical area. Strictly speaking, as long as the relative areas of the two electrodes are constant, electronic compensation of the area difference is feasible. For example, if two sources of mercury drop electrodes are used, it is only necessary to maintain the relative drop size constant. Using any of the electrochemical methods mentioned earlier for discrimination against charging currents, the arrangement according to the invention, assuming a 10% reproducibility in drop size, gives an additional order of magnitude discrimination.

Discrimination against the random noise described hereinbefore is also obtained, resulting in still further enhanced sensitivity. With the cell under potentiostatic control, a large portion of the stochastic noise voltage is caused by fluctuations of the reference electrode potential. Thus a major source of noise generated in the cell current results from the currents generated by the charging of the double layer capacitance in response to these random potential fluctuations. Since these currents are coherent in the two electrodes, the difference between the two currents does not contain these random fluctuations. Significantly, not only are these coherent random current fluctuations eliminated, but also other coherent currents generated by electrostatic or inductive pick-up as well as by ground loops are also eliminated.

Finally, the presence of large magnitude background signals are not seen in the data signal $e_d$, provided that the potential dependence of those background currents is weak. Discrimination against background is obtained, minimizing the limitation hereinbefore mentioned.

Other advantages are also derived from the invention. If the bias potential is of the order of 10 mV or less, the data signal $e_d$ will provide the derivative of the faradaic current. For example, in simple cyclic voltammetry, the derivative of the cyclic voltammogram is obtained. The zero crossing of this derivative signal can be used as a sensitive indicator or the potential of the peak anodic or cathodic current. If the peak height is desired, a simple integration of the $e_d$ not only restores the cyclic voltammogram, but also yields further discrimination against high frequency noise.

Finally, it is noted that the circuit arrangement according to the invention is also used to advantage, not only in electrochemical analytical instruments, but also in electrochemical detectors, as for example, in liquid chromatographs.

While the invention has been described in terms of an express embodiment, and alternatives have been suggested, it is clearly to be understood that those skilled in the art will effect further changes without departing from the spirit and scope of the invention as defined in the appended claims concluding the specification.

The invention claimed is:

1. In combination, an electrochemical cell having a receptacle for electrolyte, electrodes arranged in said electrolyte including:
   a counter electrode, a reference electrode, and two working electrodes;
   a pair of test signal input terminals, one of which is connected to a fixed reference potential;
   an input differential amplifier circuit having an output connected to said counter electrode, one input connected to said reference electrode, and another input connected to said other test signal input terminal;
   a signal detection circuit including:
   first and second differential amplifying circuits each having a first input terminal, a second input terminal and an output terminal;
   an output differential amplifier having a pair of input terminals and an output terminal;
   means connecting the output terminals of said first and second amplifying circuits to a different one of said pair of input terminals of said output differential amplifier;
   means connecting said first input terminal of each said first and second differential amplifying circuit to a different said working electrode;
   means connecting said second input terminal of one of said first and second amplifying circuits to said reference potential; and
   means, including a potentiometer, for connecting said second input terminal of the other of said first and second differential amplifying circuits and the other input terminal of said pair of input terminals of said output differential amplifier to said reference potential whereby the signals supplied to said output differential amplifier may be varied relative to each other by said potentiometer independently of the currents supplied to said first and second amplifying circuits from said respective working electrodes when said test signal is applied to said test signal input terminals to permit detecting any difference in currents passing between said electrolyte and said working electrodes, which difference represents a characteristic of an electroactive species in a test sample added to said electrolyte.

2. In combination, an electrochemical cell having a receptacle for electrolyte, electrodes arranged in said electrolyte including:
   a counter electrode, a reference electrode, and two working electrodes;
   a pair of test signal input terminals, one of which is connected to a fixed reference potential
   an input differential amplifier circuit having an output connected to said counter electrode, one input connected to said reference electrode, and another input connected to said other test signal input terminal;
   an output differential amplifier having a pair of input terminals and an output terminal for providing an output signal which is proportional to the difference of the signal supplied to said input terminals; and
   means for supplying to said input terminals of said output differential amplifier signals from said working electrodes developed during application of said test signal to said test input terminals, said means for supplying including means for biasing one of said working electrodes relative to said reference electrode differently than said other working electrode is biased relative to said reference electrode to cause the current signals supplied from said working electrodes to be different for each value of said test signal to thereby provide a detectable signal at the output terminal of said output differential amplifier which reflects a characteristic of an electroactive species in said electrolyte.

* * * * *